US005763210A

United States Patent [19]

Novick et al.

[11] Patent Number: 5,763,210

[45] Date of Patent: Jun. 9, 1998

[54] RECOMBINANT PRODUCTION OF INTERFERON-GAMMA BINDING PROTEINS

[75] Inventors: Daniela Novick; Yves Mory; Dina G. Fischer; Michel Revel, all of Rehovot; Menachem Rubinstein, Givat Shmuel, all of Israel

[73] Assignee: Yeda Research and Development Co. Ltd., Rehovot, Israel

[21] Appl. No.: 205,358

[22] Filed: Mar. 3, 1994

Related U.S. Application Data

[63] Continuation of Ser. No. 436,331, Nov. 14, 1989, abandoned.

[30] Foreign Application Priority Data

Nov. 14, 1988 [IL] Israel ........................... 088378

[51] Int. Cl.$^6$ ................ C07K 14/715; C12N 15/12
[52] U.S. Cl. .............. 435/69.1; 435/69.7; 435/325; 435/252.3; 435/254.11; 435/320.1; 536/23.5; 536/24.31; 530/350; 514/2
[58] Field of Search ................ 435/69.5, 69.51, 435/69.52, 320.1, 172.3, 69.1, 69.7, 252.3, 254.11, 325; 424/85.1; 536/23.52, 23.5, 24.31; 530/350; 514/8, 2

[56] References Cited

U.S. PATENT DOCUMENTS 4,897,264  1/1990  Novick et al. .................. 424/85.5

OTHER PUBLICATIONS

Mindrinos, M.N. et al. The Embo J. 147–153, (1985).
Novick et al. J. of Biol. Chem. 264(18):8483–8487 (1987) "The Human Interferon–γ Receptor".
Agult et al J. of Exp. Med 165:988–999 (1987). "Purification of Human γ Interferon Receptors . . . ".
Calderon et al. PNAS. 85:4837–4841 (1988). Purification and Characterization of hum IFN–γ receptor.
Basu et al. PNAS. 85:6282–6286 (1988). Purification and Partial Characterization of a Receptor Protein . . .
Orchansky et al. J. of Imm., 136(1):169–173 (1986) The IFN–γ Receptor in Human Monocytes is Different . . . .
Sheenan et al. J. of Imm., 140(12):4231–4237 (1988) Generation and Characterization of Monoclonal Antibodies . . . for hIFN.
Aguet et al. Cell. 55(2):273–280 "Molecular Cloning and Expression of h (FN–γ receptor".
J. Biol. Chem. 262:8483–8487, 1987, "The Human Interferon–γ Receptor, Purification, Characterization and Preparation of Antibodies", Novick et al.
J. Biol. Chem. Suppl. 12, part A:216, 1988, Two Molecular Forms of the Human Interferon–γ Receptor, Ligand Binding, Internatalization and Down Regulation, Fischer et al.
Interferon 1, I. Gresser, ed., Acad. Press, NY. 1979, pp. 53–84 "Interferons Interactions with Cell Surfaces", Friedman, R.
CRC Critical Review in Biochem. , 21:249–275, 1986. The Interferon Receptors, Rubinstein et al.
Immunol. Today, 9:393–400, 1988, "Interferon Receptors", Langer et al.

Primary Examiner—David L. Fitzgerald
Attorney, Agent, or Firm—Browdy and Neimark

[57] ABSTRACT

A cDNA encoding a new interferon-gamma (IFN-γ)-binding protein is disclosed. Methods and products for the recombinant production of the protein are provided, and specific antibodies are also described.

19 Claims, 15 Drawing Sheets

FIG. 9

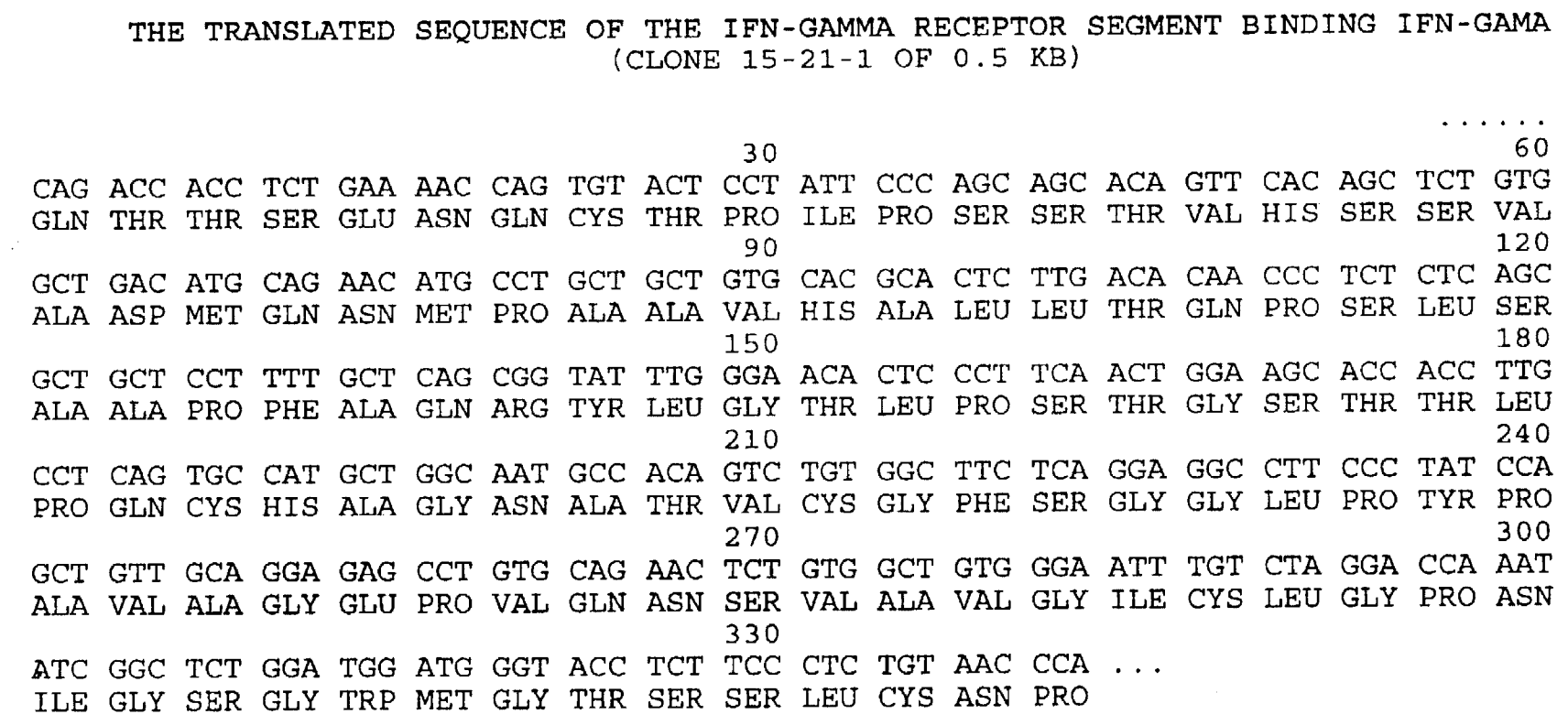

THE TRANSLATED SEQUENCE OF THE IFN-GAMMA RECEPTOR SEGMENT BINDING IFN-GAMMA
(CLONE 15-21-1 OF 0.5 KB)

```
                                                         30                                      60
CAG ACC ACC TCT GAA AAC

FIG. 10

TRANSLATED SEQUENCE OF SEGMENT OF CLONE 18-4-3 (0.7 KB) FROM IFN-GAMMA RECEPTOR

```
                                                                              . . . . . .60
CCT GAT CCT TCA GCT GAT CCC AGA TCC CAC AAA CAA GGA GCA AAA GCA CAG AAT CAA ATG
PRO ASP PRO SER ALA ASP PRO ARG SER HIS LYS GLN GLY ALA LYS ALA GLN ASN GLN MET
                                       30                                    120
ACG ACA CGT TCC ACA GGG CCA GGT GAG CTT TCT GCG GAG GGC GTG GCG GTG GTG GCA GCG
THR THR ARG SER THR GLY PRO GLY GLU LEU SER ALA GLU GLY VAL ALA VAL VAL ALA ALA
                                       90                                    180
GTT CTG GGA GAG GGA AAC CCC AGC GCC ACT TGT CTA TGG CGT GGA CGG GCA TCT CAC
VAL LEU GLY GLU GLY ASN PRO SER ALA THR CYS LEU TRP ARG GLY ARG ALA SER HIS
                                      150                                    240
                                                         210
TTT GCC GGC TCT GCG CTC CTT CTT TCC CTC CCA AAG GCT GCG GCT TTG CAT GGG
PHE ALA GLY SER ALA LEU LEU LEU PHE SER LEU PRO LYS ALA ALA ALA LEU HIS GLY
                                      270                                    300
CAG CTT GCT GCC ACT GGG CGT CCC GCA GAC TTT AAA TGG AAT GAG TGG AGG TCT ACT
GLN LEU ALA ALA THR GLY ARG PRO ALA ASP PHE LYS TRP ASN GLU TRP ARG SER THR
                                      330
GCT GCC GGA TGT AGT TCT GGA AGC TCT TGT CTC CGA TGG GGN GCT...
ALA ALA GLY CYS SER SER GLY SER SER CYS LEU ARG TRP GLY ALA
```

FIG. 11A

PARTIAL SEQUENCE OF CLONE 39 cDNA (CORRESPONDING TO 0.5 KB PROBE)

5' end:

```
<------linker sequence------->                                              60
ATG AGG ATC CCC CGG GCT GCA GGA ATT CGG GGC AAC AGT GAG AAG CAT GTG ACT TTT GAA
MET ARG ILE PRO ARG ALA ALA GLY ILE ARG GLY ASN SER GLU LYS HIS VAL THR PHE GLU
                                                                            120
AAC CAT CGC ATA GTC CCT TCA AAA AAT AGT GAT TTG AAA AAT ACC TCT CCT GAG CAT GGT
ASN HIS ARG ILE VAL PRO SER LYS ASN SER ASP LEU LYS ASN THR SER PRO GLU HIS GLY
                                        150                                 180
GGA CGT GGC TCA GAG GAT GAG CAG AGA TTC AGA CCT TCC ACG TCA CCA CTG AGT CAT
GLY ARG GLY SER GLU ASP GLU GLN ARG PHE ARG PRO SER THR SER PRO LEU SER HIS

TCT TCT......
SER SER
```

FIG. 13

PARTIAL PROTEIN SEQUENCE DEDUCED FROM CLONE 76 cDNA

```
<------linker sequence------->
MET ALA SER LEU ILE SER ASN SER GLY GLY VAL GLY HIS VAL ASP SER VAL SER LEU
LEU LEU PHE MET ILE LYS ARG ALA GLN ALA LYS ARG PHE GLY MET LYS ASN PHE LYS
LYS ARG TRP PHE ARG LEU THR ASN HIS GLU TYR HIS LYS SER LYS GLY GLU ASP GLN
PRO LEU TYR SER ILE PRO LEU ASN VAL ILE ALA VAL GLU LEU TYR ILE LEU GLN SER
PHE LYS MET ASN MET PHE GLN VAL ILE GLN PRO ILE LEU LYS SER GLN ILE CYS ALA
ASN ASN CYS VAL GLU ALA LYS ASP TRP HIS PRO SER LYS VAL SER GLN LEU CYS ASN
GLN LYS ARG LEU THR VAL TYR HIS PRO GLY CYS HIS LEU LEU TRP LEU PRO ALA ASN
ARG ALA PRO SER ASP ILE ASP GLY ARG GLU CYS THR GLY ILE TYR SER LEU PHE ASN LEU
ILE GLN LEU ASP LYS LEU GLU MET GLN GLU ALA CYS GLY ILE SER SER LYS VAL TYR ASP GLY
TYR MET SER LEU LEU GLU TYR ARG ARG PHE VAL ILE ASP ASP PRO GLN GLU THR TYR LYS THR
PRO GLU GLN GLN GLU TYR ARG ARG PHE VAL
LEU LYS GLN ...
```

FIG. 11B fragment BalI-KpnI:

```
TGT CAG GTG GGG CAT GCC ACA TCA CAC CCT GTG TCC TGC CAG GAG CCA TAT GAT GAA GAT
CYS GLN VAL GLY HIS ALA THR SER HIS PRO VAL SER CYS GLN GLU PRO TYR ASP GLU ASP   60
                                        30                                        <-BalI->                                  120

CAA AGA ATA AGT CCT AAA GAT GCT GGC AGT GAG TTC AGT GGC CAG GTT TCT
GLN ARG ILE SER PRO LYS ASP ALA GLY SER GLU PHE SER GLY GLN VAL SER              180
                    90                                        150

CAT CAG ACC ACC TCT GAA AAC TGT CCT ATT CCC AGC ACA GTT CAC AGC TCT
HIS GLN THR THR SER GLU ASN CYS PRO ILE PRO SER THR VAL HIS SER SER              240
                                        210

GTG GCT GAC ATG CAG AAC ATG CCT GCT GTG CAC CTC TTG ACA CAA CCC TCT CTC
VAL ALA ASP MET GLN ASN MET PRO ALA VAL HIS LEU LEU THR GLN PRO SER LEU          300
                                270

AGC GCT GCT CCT TTT GCT CAG TAT CGG AAT GCC TTG GGA ACA CTC CCT TCA ACT GGA AGC ACC
SER ALA ALA PRO PHE ALA GLN TYR ARG ASN ALA LEU GLY THR LEU PRO SER THR GLY SER THR  360
                                        330

TTG CCT CAG TGC CAT GCT GGC CAT GCT GTC TGT GGC TTC TCA GGA GGC CTT CCC TAT
LEU PRO GLN CYS HIS ALA GLY HIS ALA VAL CYS GLY PHE SER GLY GLY LEU PRO TYR      420
                                        390

CCA GCT GTT GCA GGA GAG CCT GTG CAG GTG GCT GTG ATT TGT CTA GGA TCA
PRO ALA VAL ALA GLY GLU PRO VAL GLN VAL ALA VAL ILE CYS LEU GLY SER
                                <KpnI->  450

AAT ATC GGC TCT GGA TGG ATG GGT ACC TCT TCC CTC TGT AAC CCA TAT TCT AAT ACC
ASN ILE GLY SER GLY TRP MET GLY THR SER SER LEU CYS ASN PRO TYR SER ASN THR
```

FIG. 12

NUCLEOTIDE SEQUENCE OF CLONE 76 cDNA (CORRESPONDING TO 0.7 KB PROBE)

```
<------linker----------->   30          40          50          60
ATGGCAAGCT  TGATATCGAA  TTCGGGCGGG  GTTGGTGGAC  ACGTGGATTC  CGTGTCTTTG
    70          80          90         100         110         120
CTGTTGTTCA  TGATCAAGAG  GGCCCAAGGA  CGGAAGCGCT  TTGGGATGAA  GAATTTTAAG
   130         140         150         160         170         180
AAGAGATGGT  TTCGCTTGAC  CAACCATGAA  TTTACCTACC  ACAAAAGCAA  AGGGGACCAG
   190         200         210         220         230         240
CCTCTCTACA  GCATTCCCAT  CGAGAACATC  CTGGCAGTGG  AGAAGCTGGA  GGAGGAGTCT
   250         260         270         280         290         300
TTCAAAATGA  AAAACATGTT  CCAGGTCATC  CAGCCAGAGC  GTGCGCTGTA  CATCCAGGCC
   310         320         330         340         350         360
AACAACTGCG  TGGAGGCCAA  GGACTGGATC  GACATTCTCA  CCAAAGTGAG  CCAGTGCAAC
   370         380         390         400         410         420
CAGAAGCGCC  TCACCGTCTA  CCACCCGTCC  GCCTACCTGA  GCGGCCACTG  GCTGTGCTGT
   430         440         450         460         470         480
AGGGCGCCAT  CCGACTCGGC  TCCGGGCTGC  TCGCCCTGCA  CTGGCGGCCT  CCCAGCCAAC
   490         500         510         520         530         540
ATCCAGCTGG  ACATTGATGG  GGACCGTGAG  ACGGAGCGTA  TCTACTCCCT  CTTCAACTTG
   550         560         570         580         590         600
TACATGAGCA  AGCTGGAGAA  GATGCAGGAG  GCCGTGGGA   GCAAATCTGT  GTATGACGGC
   610         620         630         640         650         660
CCGGAGCAGG  AGGAGTATCG  ACGTTTCGTC  ATTGACGACC  CCCAGGAGAC  CTACAAGACG
   670         680         690         700         710         720
CTAAAGCAGT  CATCGCTGGG  GTTGGGGCTT  TGGAGCAGGA  GCACGCCCAG  TATAAGAGGG
   730         740         750         760         770         780
ACAAGTTCAA  GAAGACGAAA  TATGGAAGCC  AGGAGCACCC  CATCGGAGAC  AAGAGCTTCC
   790         800         810         820    Aha3 830         840
AGAACTACAT  CCGGCAGCAG  TCCGAGACCT  CCACTCATTC  CATTTAAAGT  CTGCGGGACG
   850         860         870         880         890         900
CCCAGTGGCA  GCAAGCTGCC  CATGCAAAGC  CGCAGCCTTT  GGGAGGGAGA  AGAGAAGGAA
   910         920         930         940         950         960
GAGCGCAGAG  CCGGCAAAGT  GAGATGCACG  CCGTCCCGCC  CATAGACAAG  TGGCGCTGGG
   970         980         990        1000        1010        1020
GTTTCCCTCT  CCCAGAACCG  CTGCCACCAC  CGCCACGCCC  TCCGCAGAAA  GCTCACCTGG
  1030        1040        1050        1060        1070        1080
CCCTGTGGAA  CGTGTCGTCA  TTTGATTCTG  TGCTTTTTGC  TCCTTGTTTG  TGGGGATCTG
  1090        1100        1110        1120        1130        1140
GGGATCAGCT  GAAGGATCAG  GAAGTGTGGG  CTGTGCTAGC  CACACCACAG  CCAGCCTCAG
  1150        1160 SalI  1170        1180        1190        1200
GGAGCCACTT  CCCGTCTAGT  CGACTGTGAC  ATGCACCTCC  GGCCGTGTGT  GCATCAGTCT
  1210        1220        1230        1240        1250        1260
CGTGCACGTC  TGTCTTGCGT  GCACGGTGCG  TGTGACGCTG  GGCTCTGTGG  CTCTGTGCCC
  1270        1280        1290        1300        1310        1320
GGGAGCCTGC  TGGCCCGCCT  CGGCTTTCGG  CTTCATCACA  TTGGGAGGTT  CAGAGCATTA
  1330        1340        1350        1360        1370        1380
CTCTCCCACT  GTGCCTGCCA  TCCAGGCAGC  CATGGGAGGC  GGCCTCCCTG  TTCCACTTTC
  1390        1400        1410        1420        1430        1440
GAGGTTCGTT  TGATTCCTGG  CTGAGGGGTC  AGTTTTATGG  CTGGGAGGTG  CAGAACTACA
  1450        1460        1470        1480        1490        1500
CAGAAGTCCC  AGTCTGAGGA  TGTCCTTGGT  GCTTGGGGGA  TACGGGTTCT  GTCCACAGAG
  1510        1520        1530        1540        1550        1560
TCCCTTGGAG  GGAAAGGTGT  AGGCTCCAGC  TTCTCCAGGC  GTCTGCGGAC  CCACAGTTGA
  1570        1580        1590        1600        1610
AGCCCACACG  TTTTGCTGTT  GAATGGGGTT  TAAAATCAGA  ATTAACATTT  GCCACCCCC...
                                  Aha3
```

ID # RECOMBINANT PRODUCTION OF INTERFERON-GAMMA BINDING PROTEINS

This application is a continuation of application Ser. No. 07/436,331, filed Nov. 14, 1989 now abandoned.

BACKGROUND OF THE INVENTION

1. Field of the Invention

The present invention relates to proteins having interferon-gamma (IFN-gamma) binding activity, to proteins substantially homologous therewith or fragments thereof, to DNA molecules, in particular cDNA molecules, encoding these proteins or fragments thereof, and to monoclonal antibodies to the human IFN-gamma receptor used for isolating said cDNA clones. The invention further relates to the cloning of said human IFN-gamma binding proteins and their production by recombinant DNA techniques and to pharmaceutical compositions comprising them.

2. Description of the Background Art

Interferon-gamma is a lymphokine produced by activated T-lymphocytes. It exerts antiviral activity, growth inhibitory effect and several immunoregulatory activities on a variety of cell types and is of potential clinical value. However, together with its positive biological activities, IFN-gamma has been shown to provoke undesirable effects and to be involved in the development of autoimmune diseases. Thus, IFN-gamma was present in newly diagnosed diabetic children and in muscle biopsies from patients with polymyositis. It was also found to cause exacerbation of autoimmune diseases such as multiple sclerosis and psoriasis.

It is therefore desirable to find ways to eliminate or antagonize the undesirable activities or effects of IFN-gamma endogenously formed in excess or exogenously administered, and particularly to block its action, or controlling the progression of autoimmune processes.

In commonly assigned European Patent Application Publ. No. 240975 and U.S. Ser. No. 07/030,640, now U.S. Pat. No. 4,897,264, whose contents are herein incorporated by reference, IFN-gamma receptors having different molecular weight ranges were isolated from different cells by extraction followed by affinity chromatography on an immobilized IFN-gamma column. In the same application polyclonal antibodies to the FIN-gamma receptors were described.

SUMMARY OF THE INVENTION

In one aspect, the invention relates to proteins having IFN-gamma binding activity or proteins substantially homologous therewith or fragments thereof, said proteins comprising the amino acid sequence shown in FIG. 9 or FIG. 13. The invention encompasses larger proteins wherein these amino acid sequences are part of the total sequence of the protein molecule as well as fragments comprising essentially only part of said amino acid sequences. Substantially homologous proteins or fragments thereof are included with the scope of the invention provided that they show the same biological activity of the proteins of the invention.

In another aspect, the present invention relates to the use of monoclonal antibodies against human IFN-gamma receptor, in particular the IFN-gamma receptor of non-immune cells, e.g. WISH, HeLa or FS-11 cells, having a molecular weight of about 90,000 da, in isolating such proteins.

The invention further relates to DNA molecules comprising a recombinant DNA molecule or a cDNA molecule comprising the nucleotide sequence coding for the proteins of the invention or fragments thereof, to replicable expression vehicles comprising them and host cells transformed therewith, and to a process for producing said proteins or fragments thereof by culturing said transformant cells in a suitable culture medium and harvesting the protein on a fragment thereof either from the cells or from the culture supernatant.

BRIEF DESCRIPTION OF THE DRAWINGS

FIG. 9 shows the nucleotide sequence of the 0.5 kb cDNA segment and its translated amino acid sequence.

FIG. 10 shows the nucleotide sequence of the complementary strand of the 0.7 kb cDNA segment and its translated amino acid sequence.

FIGS. 11A–B show two partial nucleotide and translated amino acid sequences of the 1.8 kb cDNA segment.

FIG. 12 is a partial nucleotide sequence of the 2.3 kb cDNA.

FIG. 13 is a partial translated amino acid sequence corresponding to FIG. 12 above.

DETAILED DESCRIPTION OF THE PREFERRED EMBODIMENTS

Figure 1:
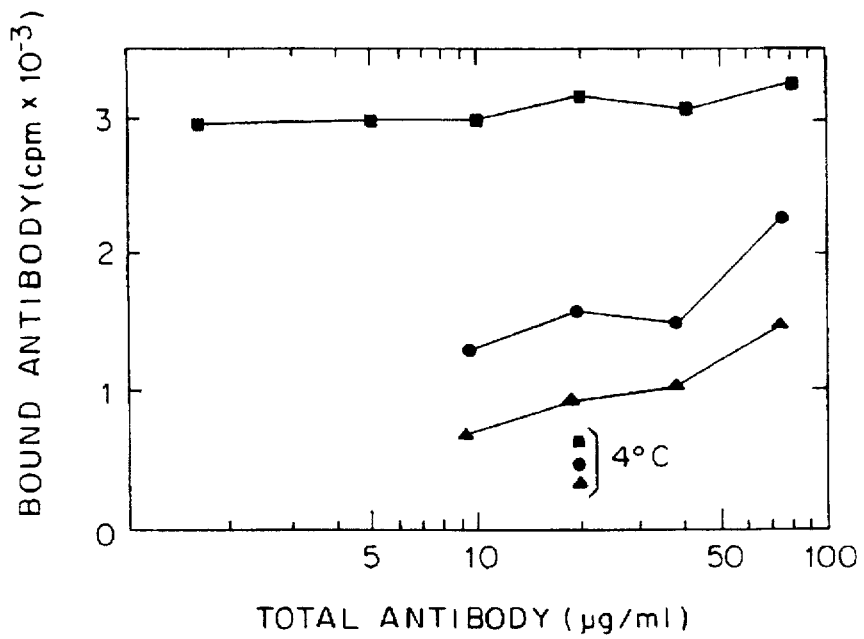
FIG. 1 shows a comparison of the binding capacity of monoclonal antibodies 37-1, 183-2 and 177-1 for HeLa cells.

According to the invention, cDNA clones encoding a portion of the human IFN-gamma binding proteins were isolated with the aid of monoclonal antibodies to the human IFN-gamma receptor. These antibodies were characterized by their ability to block the binding of $^{125}$I-IFN-gamma to its receptor on human cells. A cDNA HeLa expression library in lambda gt 1 was screened by the antibodies and 5 positive clones were obtained from $10^6$ recombinants. Four of the clones had an insert of 0.5 Kb and one was of 0.7 Kb. The 0.5 Kb fragments cross hybridized, but did not hybridize to the 0.7 Kb clone, as determined by Southern blots. The inserts were ligated to a Bluescript plasmid vector and E. coli TG1 competent bacteria were transformed. Colonies containing the inserts from two of the clones (0.5 Kb and 0.7 Kb) were further grown and the single-stranded DNA obtained with the aid of a helper virus was used for sequencing. One open-reading frame was revealed in the sequencing and no significant homology to known DNA sequences was observed. FIG. 9 shows the nucleotide sequence of clone 15-21-1 of 0.5 Kb and FIG. 10 shows the nucleotide sequence of the complementary strand of clone 18-4-3 of 0.7 Kb.

The proteins encoded by the inserts were isolated and characterized. Lysogens were prepared and the induced proteins were purified by anti-IFN-gamma receptor immunoadsorbent. The size of the proteins in the eluted fractions was determined by SDS-PAGE followed by silver staining and by Western blotting. The fused protein originating from the 0.5 Kb clone had a Mr of about 130,000 (Mr of β-galactosidase=114,000). Binding of $^{125}$I-IFN-gamma to the fused protein was demonstrated in solution and was inhibited by an excess of unlabeled IFN-gamma. No such binding was detected with β-galactosidase alone. Cross-linking experiments of $^{125}$I-IFN-gamma to this fused protein followed by immunoprecipitation resulted in a complex of Mr=155,000 (Mr of IFN-gamma is 25,000), as visualized by SDS-PAGE and autoradiography. This indicates that this 0.5 Kb cDNA fragment is coding for at least part of the ligand binding domain of a human IFN-gamma binding protein.

Probes were prepared from the 0.5 Kb and 0.7 Kb inserts and a cDNA human placenta library in lambda gt11 was screened. Ten positive clones were obtained from $10^6$ recombinants. Nine of the clones had an insert size of 1.15–2.3 Kb and they all cross hybridized, while one of the clones had an insert size of 1.8 Kb and it hybridized only to itself. Two clones of 1.8 Kb and 2.3 Kb were linked to expression vehicles, transferred into bacterial cells and the proteins encoded by them were expressed.

Other probes may be prepared from the cDNA sequences of the invention and used for screening any cDNA library, e.g., colon, liver or kidney library or for isolation of the genomic DNA coding for the proteins of the invention by known methods, e.g. by colony hybridization techniques under stringent conditions. Positive clones are then inserted into appropriately constructed expression vectors by techniques well known in the art. Double-stranded cDNA is linked to plasmid vectors by homopolymeric tailing or by restriction linking involving the use of synthetic DNA linkers or blunt-ended ligation techniques. DNA ligases are used to ligate the DNA molecules and undesirable joining is avoided by treatment with alkaline phosphates.

In order to be capable of expressing a desired protein, an expression vector should comprise also specific nucleotide sequences containing transcriptional and translational regulatory information linked to the DNA coding for the desired protein in such a way as to permit gene expression and production of the protein. The gene must be preceded by a promoter in order to be transcribed. There are a variety of such promoters in use, which work with different efficiencies (strong and weak promoters).

The DNA molecule comprising the nucleotide sequence coding for a protein of the invention or a fragment thereof preceded by a nucleotide sequence of a signal peptide and the operably linked transcriptional and translational regulatory signals is inserted into a vector which is capable of integrating the desired gene sequences into the host cell chromosome. The cells which have stably integrated the introduced DNA into their chromosomes can be selected by also introducing one or more markers which allow for selection of host cells which contain the expression vector.

In a preferred embodiment, the introduced DNA molecule will be incorporated into a plasmid or viral vector capable of autonomous replication in the recipient host. Factors of importance in selecting a particular plasmid or viral vector include the ease with which recipient cells that contain the vector may be recognized and selected from those recipient cells which do not contain the vector; the number of copies of the vector which are desired in a particular host and whether it is desirable to be able to "shuttle" the vector between host cells of different species. Once the vector or DNA sequence containing the construct(s) has been prepared for expression, the DNA construct(s) may be introduced into an appropriate host cell by any of a variety of suitable means: transformation, transfection, conjugation, protoplast fusion, electroporation, calcium phosphate precipitation, direct microinjection, etc.

Host cells to be used in this invention may be either prokaryotic or eukaryotic. Preferred prokaryotic hosts include bacteria, such as E. coli. Under such conditions, the protein will be by glycosylated. The prokaryotic host must be compatible with the replicon and control sequences in the expression plasmid.

Preferred eukaryotic hosts are mammalian cells, e.g., human, monkey, mouse and chinese hamster ovary (CHO) cells, because the provide post-translational modifications to protein molecules including correct folding or glycosylation at correct sites. Also yeast and insect cells can carry out post-translational peptide modifications including glycosylation. A number of recombinant DNA strategies exist which utilize strong promoter sequences and high copy number of plasmids which can be utilized for production of the desired proteins in yeast. Yeast recognizes leader sequences on cloned mammalian gene products and secretes peptides bearing leader sequences (i.e. pre-peptides).

After the introduction of the vector, the host cells are grown in a selective medium, which selects for the growth of vector-containing cells. Expression of the cloned gene sequence(s) results in the production of the desired protein or a fragment thereof. The expressed protein is then isolated and purified by any conventional procedure involving extraction, precipitation, chromatography, electrophoresis, or the like.

The monoclonal antibodies against the human IFN-gamma receptor provided by the invention are useful for the purification of the receptor and for isolation of the cDNA clones of the invention. They bind IFN-gamma and inhibit its biological activity, thus differing from prior art monoclonal antibodies (Agust, M. and Merlin, G. (1987) J. Exp. Med. 165, pp. 988–999) not reported to inhibit IFN-gamma biological activity.

The monoclonal antibodies against the human IFN-gamma receptor of the invention were developed by injecting mice with a preparation of receptor which was purified from solubilized placental membranes by ligand affinity chromatography. Three antibodies were identified by their ability to block the binding of $^{125}$I-IFN-gamma to its receptor on HeLa cells at 4° C. One of these antibodies blocked several biological activities of IFN-gamma, including its antiviral activity, its ability to induce HLA-DR surface antigens and its ability to protect cells from NK-cell mediated cytotoxicity. This antibody exhibited higher binding capacity to cells at 37° C. and was significantly less displaceable by an excess of IFN-gamma as compared with the other two antibodies. Immunoaffinity chromatography of solubilized crude placental membrane preparation yielded a purified receptor which exhibited a molecular weight of about 88,000. The purified receptor retained its ability to bind $^{125}$I-IFN-gamma in solution.

The invention is illustrated by, but not limited to, the following examples:

EXAMPLE 1
Immunization of Mice and Cell Fusion

BALB/c mice were immunized subcutaneously with a preparation of human IFN-gamma receptor obtained from placental membranes. This preparation was purified on IFN-gamma coupled to Affigel 10, then on Sephacryl S-300 (Novick, D. et al (1987) J. Biol. Chem. 262, p.8483) and finally adsorbed on agarose beads coupled to monoclonal anti-IFN-gamma antibodies (Novick, D. et al (1983) EMBO J. 2, p. 1527). Two injections were given in complete Freund's adjuvant and the other two were given in 1 week intervals without an adjuvant. Each mouse received ~30 μg of affinity purified receptor per injection. The last boost was given intraperitoneally 4 days before fusion. Sere were checked for their ability to block the binding of $^{125}$I-IFN-gamma to HeLa cells as described hereinafter. Spleen cells ($200\times10^6$) from a mouse exhibiting a titer of 1:500 in this assay were fused with $40\times10^6$ NBO/1 myeloma cells. Hybridomas were selected in Dulbecco's modified Eagle's medium, supplemented with 1 mM pyruvate, 2 mM glutamine, penicillin (10 units/ml), streptomycin 20 μg/ml, fungizone 250 μg/ml, 10% fetal bovine serum (FBS), and containing HAT. Hybridomas that were found to secrete anti-IFN-gamma receptor antibodies were cloned by the limiting dilution method.

EXAMPLE 2
Tests for Screening of Hybridoma Supernatants

Hybridoma supernatants were tested for the presence of anti-IFN-gamma receptor antibodies both competitive inhibition of binding of $^{125}$I-IFN-gamma to HeLa cells and by neutralization of antiviral activity of IFN-gamma on WISH cells.

a) Inhibition of $^{125}$I-IFN-gamma binding to cells by anti-receptor antibodies: HeLa cells (ATCC H229, CCL2.1) were seeded in 96-well microtiter plates (50,000 cells/well) in the presence of dexamethasone ($10^{-6}$M). After 24 hrs, medium was discarded, cells were washed with ice cold phosphate-buffered saline containing $Ca^{2+}$, $Mg^{2+}$ (PBS) and sodium azide (0.02%). Hybridoma supernatants (50 μl/well) were added, and the plates were left for 2 hours at 4° C. Following two washings with ice cold PBS containing 2% FBS and 0.02% sodium azide (PBS-2%), $^{125}$I-IFN-gamma produced by CHO cells, purified by affinity chromatography and labeled by the known chloramine-T method, was added to each well (50 μl, 200,000 cpm) and the plates were left for 2 hrs at 4° C. The plates were then washed 4 times with PBS 2%, harvested with NaOH (0.75M, 125 μl) and the content of each well was counted.

A competitive inhibition of binding was performed in 24-well plates (Costar) on HeLa cells (250,000 cells/well without dexamethasone). The assay was done in the same manner as described for the one in 96 well microtiter plates, except for the volumes (250 μl of serially diluted hybridoma supernatants and 250 μl of $^{125}$I-IFN-gamma, 200,000 cpm). Cells were harvested with trypsin (250 μl), the wells were further washed with PBS ($2\times150$ μl) and the combined cells and washings were counted.

b) Neutralization of interferon-gamma activity: Hybridoma supernatants (50 μl) were added to cultures of WISH cells (ATCC CCL25) in 96-well plates, incubated for 2 hours at 37° C. and followed by the addition of IFN-gamma (20 U/ml, 50 μl). The plates were incubated overnight at 37° C., vesicular stomatitis virus was added, the plates were further incubated overnight and the extent of the cytopathic effect was determined by staining with crystal violet (Rubinstein et al. (1981) J. Virol. 37, p. 755). For determination of neutralizing titer, hybridoma supernatants (or ascitic fluids) were serially diluted prior to the neutralization assay. One neutralizing unit is defined as the amount of antibody sufficient for neutralizing one unit of IFN-gamma. The NIH reference standard of IFN-gamma Gg23-901-503 was used in all assays.

EXAMPLE 3
Screening of the Hybridomas

Hybridoma supernatants were screened for the presence of anti IFN-gamma receptor antibodies as described above. Three out of 468 hybridomas screened were found to inhibit the binding of $^{125}$I-IFN-gamma to HeLa cells, and one out of the three was also positive in the neutralization assay. The positive clones were further grown and subcloned, and the cells were injected into mice for generation of ascitic fluids. The immune response in mice, the screening and the extent of antibody production in tissue culture and in ascitic fluids were all followed both by the binding assay (Table I) and by the neutralization assay (Table II).

From the three monoclonal antibodies against the human interferon-gamma receptor developed here, antibody No. 177 and all its subclones were characterized by their ability to bind specifically to a solubilized IFN-gamma receptor, to inhibit the binding of $^{125}$I-IFN-gamma to cells (at 4° C.), to block the antiviral activity of IFN-gamma and the induction of HLA-DR by IFN-gamma and to prevent the induction of resistance to NK-CMC by IFN-gamma. Two other monoclonal antibodies (Nos. 37 and 183) inhibited the binding of $^{125}$I-IFN-gamma to cells at 4° C. but were unable to block the biological activities of IFN-gamma. All biological activities were determined at 37° C. Since binding is a prerequisite to biological activity, antibody No. 177 was tested to see whether it had a higher affinity for the receptor as compared with the other two antibodies and whether IFN-gamma could displace the antibodies from the receptor at 37° C.

TABLE I

Inhibition of $^{125}$I-IFN-gamma to HeLa cells by anti-receptor antibodies.

| Sample | Inhibiton in microplates | | | Inhibition in 24-well plates | | |
|---|---|---|---|---|---|---|
| | antibody dilution | cpm | % | antibody dilution | cpm | % |
| Immune serum (mouse) | 1:500 | 50 | 83 | 1:500 | 550 | 61 |
| Neg. control serum | 1:500 | 350 | 0 | 1:500 | 1400 | 0 |

TABLE I-continued

Inhibition of $^{125}$I-IFN-gamma to HeLa cells by anti-receptor antibodies.

| Sample | Inhibiton in microplates | | | Inhibition in 24-well plates | | |
|---|---|---|---|---|---|---|
| | antibody dilution | cpm | % | antibody dilution | cpm | % |
| Hybridoma 37^ | undiluted | 112 | 68 | 1:100 | 250 | 83 |
| | | | | 1:2500 | 890 | 40 |
| Hybridoma 177^ | undiluted | 76 | 78 | 1:50 | 900 | 39 |
| | | | | 1:250 | 1080 | 27 |
| Hybridoma 183^ | undiluted | 96 | 73 | 1:250 | 370 | 75 |
| | | | | 1:1250 | 1020 | 31 |
| Negative hybridoma | undiluted | 350 | 0 | — | 1475 | 0 |
| Ascitic fluid 183-2 immunoglobulins (16 mg/ml) | | | | 1:200000 | 560 | 62 |

^Hybridoma supernatants from the first screen were tested once in microplates, whereas supernatants of positive clones that were grown in larger amounts were tested in triplicates in 24 well plates. In the latter case the counts ranged within ±15%.

Indeed it was found that the two other antibodies could be displaced from cell surface by an excess of IFN-gamma whereas almost no such displacement of antibody No. 177 was observed. It is noteworthy that none of the antibodies exhibited antiviral activity or HLA-DR inducing activity when incubated with cells in the absence of IFN-gamma.

Hybridoma 177-1, subcloned from hybridoma 177, was deposited on 14.11.1988 with the Collection Nationale de Cultures de Micro-organismes CNCM I-814.

EXAMPLE 4
Binding of Anti-Receptor Antibodies to Cells

The three monoclonal antibodies No. 37, 177 and 183, inhibited the binding of $^{125}$I-IFN-gamma to cells at 4° C. The test was done as described in Example 2a. The results are shown in Table I. However, only antibody 177-1 inhibited the biological activities of IFN-gamma. Therefore comparative binding studies were performed at 37° C. in the presence of sodium azide (to prevent internalization). Antibody 177-1 had a significantly higher binding capacity to cells as compared with the other two antibodies. This is shown in FIG. 1, where HeLa cells were incubated at 37° C. (in the presence of NaN$_3$) with monclonal antibody No. 37-1 (●—●), 183-2 (▲—▲) and 177-1 (■—■); followed by $^{125}$I-goat anti-mouse serum. Background counts (in the absence of anti-receptor antibody, 200 cpm) were subtracted. Binding at 4° C. with 20 µg/ml of the various antibodies is shown as well.

Figure 2:
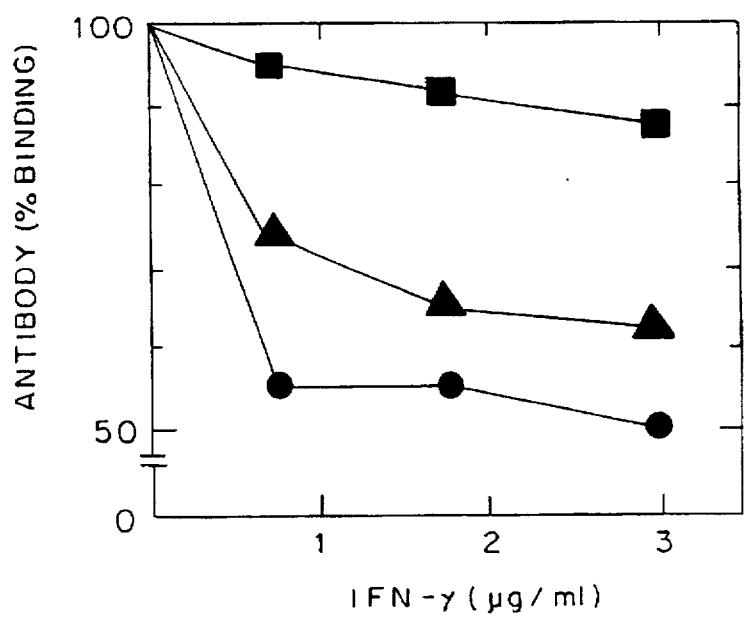
FIG. 2 shows a comparison of the inhibitory effect of IFN-gamma on the binding of monoclonal antibodies 37-1, 183-2 and 177-1 to HeLa cells.

Subsequent addition of IFN-gamma caused a significant displacement of the bound antibodies No. 37-1 and 183-2 and only minimal displacement of the neutralizing antibody No. 177-1. The inhibition of the binding of anti-receptor antibodies by IFN-gamma at 37° C. is shown in FIG. 2, where HeLa cells were incubated with anti-receptor antibody no. 37-1 (●—●, 30 µg/ml), 183-2 (▲—▲, 30 µg/ml) or 177-1 (■—■, 1.6 µg/ml), together with various concentrations of IFN-gamma. The cells were then washed and incubated with $^{125}$I-goat anti-mouse serum. Maximal binding gave 3500 cpm. Background counts (in the absence of anti-receptor antibodies, 250 cpm) were subtracted.

Figure 3:
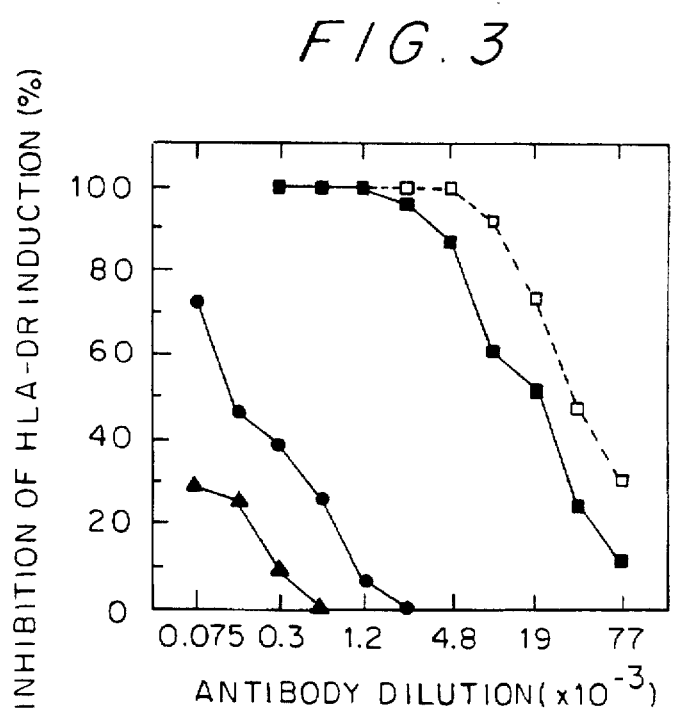
FIG. 3 shows a comparison of the ability of monoclonal antibodies 37-1, 183-2, 177-1, and 166-5 to block the induction of HLA-DR antigens in HeLa cells by IFN-gamma.

EXAMPLE 5
The Antiviral Activity and the IFN-gamma induced HLA-DR Expression are Blocked by the Monoclonal Antibodies All subclones of antibody No. 177 blocked the antiviral activity of IFN-gamma. The neutralizing titer of the various subclones ranged for 4000–30,000 units/ml. No such blocking activity was observed with the other two antibodies. The results are shown in Table II. In a control study none of these antibodies were found to block the antiviral activity of IFN-gamma. None of the antibodies had an intrinsic capacity to elicit an antiviral state in the cells. The anti-receptor monoclonal antibodies were tested for their ability to block the induction of HLA-DR antigens in HeLa cells by IFN-gamma. Once again antibody No. 177-1 (■—■) exhibited high blocking activity and 50% inhibition was observed at ascitic fluid dilution of 1:20,000. Antibodies 37-1 (●—●) and 183-2 (▲—▲) exhibited only a marginal blocking effect (FIG. 3). Incubation of HeLa cells with any of the three antibodies in the absence of IFN-gamma did not induce HLA-DR antigens. As a positive control the neutralizing monoclonal anti-IFN-gamma antibody No. 166-5 (□—□) described in Novick, D. et al (1983) EMBO J. 2, p. 1527 was used. It inhibited the IFN-gamma induced HLA-DR, whereas no such inhibition was observed with a monoclonal anti-IFN-gamma antibody No. 7 described in Novick, D. et al (1982) J. Immunol. 129, p. 2244 (not shown). The maximal induction of HLA-DR (in the absence of antibodies) was 2700±100 cpm. Basal level (in the absence of IFN-gamma) was 200 cpm and was subtracted from all readings.

TABLE II

Neutralization of IFN-gamma activity in WISH cells by anti-receptor antibodies.

| Sample | Titer (units/ml) |
|---|---|
| Immune serum (mouse) | 35000 |
| Control serum | <60 |
| Hybridoma 37 | <60 |
| Hybridoma 177 | 2000 |
| Hybridoma 177-1^ | 4000 |
| Hybridoma 177-10^ | 30000 |
| Hybridoma 183 | <60 |
| Ascitic fluid 177-10^ | 60000 |

^A subclone of antibody No. 177.

The inhibition of IFN-gamma class II MHC antigens (HLA-DR) by anti-receptors antibodies was performed as follows: HeLa cells (5×10$^4$ cells/wall) were seeded in 96-well plates and incubated for 3 hrs at 37° C. in RPMI 1640 medium (100 µl, containing 1% FBS, RPMI-1%). Various monoclonal antibodies were added in serial two-fold dilutions (in 50 µl RPMI-1%), and the plates were further incubated at 37° C. for 3 hrs. IFN-gamma (60 units/ml, 50 µl, RPMI-1) was then added and the plates were further incubated for 40 hours at 37° C. The plates were then washed with cold PBS (3×100 µl), and fixed with formaldehyde (3.5% in PBS, 100 µl) for 30 min at 0° C. The plates were then rinsed with cold PBS and incubated with a solution of BSA (100 µl, 0.5% in 5 mM Tris-HCl, 150 mM NaCl, pH7.5) for 30 min at 0° C. The plates were then rinsed with cold PBS and incubated for 1 hr at room temperature with monoclonal anti HLA-DR (L-243 ascitic fluid diluted 1:500 in 50 µl RPMI-1640 medium containing 0.1% BSA and 0.1% sodium azide). The plates were then rinsed with PBS and incubated for 30 minutes at room temperature with $^{125}$I-protein A (10$^5$cpm/well in 50 µl RPMI-1640 medium containing 0.1% BSA and 0.1% sodium azide). Excess of radioactivity was removed by washing with PBS containing 0.05% Tween 20 (3×200 µl). The cells were then solubilized with NaOH (0.75 Nm 200 µl) and counted.

The binding of anti-receptor antibodies to cells at 37° C. and competition by IFN-gamma was performed as follows: HeLa cells ($3 \times 10^5$/well) were seeded and grown for 24 hours at 37° C. in 24 well plates. Medium was discarded, various concentrations of anti-receptor antibodies (250 µl, in RPMI containing 10% FBS and 0.04% sodium azide) were added together with IFN-gamma (0–6 µg/ml) and the plates were incubated for 3 hrs. Following two washings with PBS-2%, $^{125}$I-goat anti mouse serum (250 µl, 100,000 cpm) was added. The plates were left for 5 hrs at room temperature, washed with PBS-2% (3×1 ml), harvested with trypsin and counted.

EXAMPLE 6
Inhibition of IFN-gamma Induced Anti-NK Effect by Anti-Receptor Antibodies Resistance to natural killer cell mediated cytotoxicity (NK-CMC) induced by IFN-gamma was prevented by incubation of the target cells U-937 (ATCC CRL1593) with F(ab')$_2$ fragments prepared from antibody No. 177-1 together with IFN-gamma.

Figure 4:
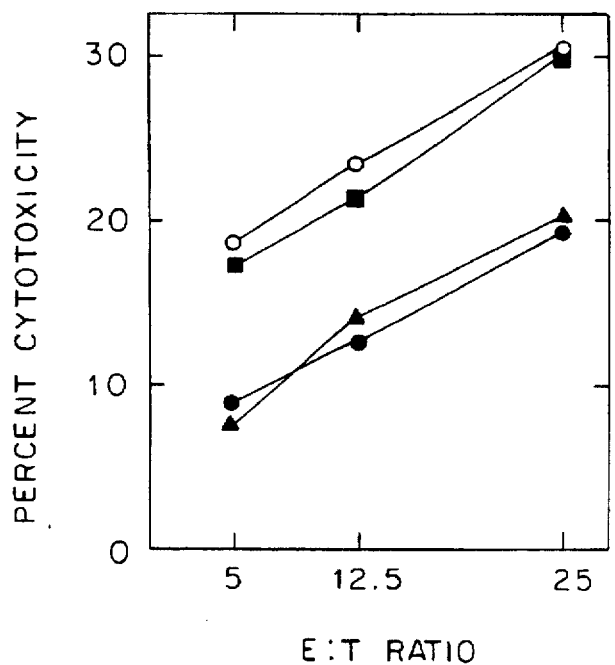
FIG. 4 shows a comparison of the ability of monoclonal antibodies 37-1 and 177-1 to prevent induction of resistance to natural killer cell-mediated cytotoxicity in U-937 cells by IFN-gamma.

The prevention was dose-dependent and was apparent in several effector cell: target cell ratios (E:T). No such inhibition was observed when antibody 37-1 or its F(ab')$_2$ portion were incubated with the target cells. A similar extent of inhibition of IFN-gamma-treated U-937 target cells by the anti-receptor antibodies (177-1) was obtained when the NK effector cells were activated by preincubation with IFN-alpha (data not shown). The results of the inhibition of IFN-gamma-induced anti NK effect by anti- receptor antibody are shown in FIG. 4, where U-937 cells were preincubated with anti-receptor antibodies No. 37-1 (▲—▲), 177-1 (■—■) or no antibody (●—●) followed by addition if IFN-gamma. Control cells were not treated with IFN-gamma(○—○). The cells were then labeled with [$^{51}$Cr]-Na$_2$CrO$_4$ and mixed with effector cells at the indicated E:T ratios. Spontaneous cytotoxicity was less than 6%.

The blocking of IFN-gamma induced resistance to NK cell-mediated cyto- xicity by anti-receptor antibody was tested as follows: U-937 target (T) cells ($3.5 \times 10^5$) were preincubated for 3 hr at 37° C. with or without monoclonal anti-receptor antibody (50–100 ng in 750 µl RPMI 1640 medium containing 10% FBS). IFN-gamma (1000 units in 250 µl medium) was added and incubation was further continued for 9 hrs. The cells were then labelled with $^{51}$[Cr]Na$_2$CrO$_4$ (0.5 mCi, 1.5 hr), washed and incubated in triplicates ($10^4$ cells, 50 µl/well) for 4 hrs at 37° C. with the effector cells 100 µl/well) at the indicated E:T ratios. The cells were then spun and the supernatant was counted (C). Spontaneous release (S: up to 6% of total cpm) was measured in supernatant of target cells alone and total cpm (T) was measured by adding Triton X-100 (1%, 100 µl) to labelled target cells. Percent cytotoxicity was determined according to the formula:

$$\% \text{ cytotoxicity} = 100 \times \frac{C-S}{T-S}$$

EXAMPLE 7
Preparation of Immunoadsorbent and Immunoaffinity Chromatography of Placental IFN-gamma Receptor Preparations An immunoadsorbent was prepared from an immunoglobulin fraction of ascitic fluids of mice containing monoclonal antibodies secreted by the hybridomas of the invention (e.g. of hybridomas 177 or 183). The ascitic fluids were precipitated with ammonium sulfate at 4° C. (final concentration 50% saturation). The precipitate was collected by centrifugation, redissolved in water and dialysed against saline. About 10 mg of immunoglobulins were bound to polyacrylic hydrazide-agarose (Biomakor).

A solubilized placental membrane preparation was loaded to the antibody column at 4° C. at a flow rate of 0.2 ml/min. The column was washed with PBS containing 0.1% Triton X-400 (40 ml) and eluted by citric acid (50 mM, pH2) containing 0.05% Triton X-100 and 0.02% sodium azide. Eluted fractions were neutralized by Hepes Buffer (1M, pH 8.5) and kept at 4° C. The column was monitored by binding of radiolabeled IFN-gamma and a purification of 4250 fold was achieved in one step (Table III). Analysis of the purified receptor preparation by SDS-PAGE using 7.5% polyacrylamide gel under reducing conditions and silver staining revealed the presence of a major band corresponding to a molecular weight of about 88,000. This purified IFN-gamma receptor retained its binding activity.

Figure 5:
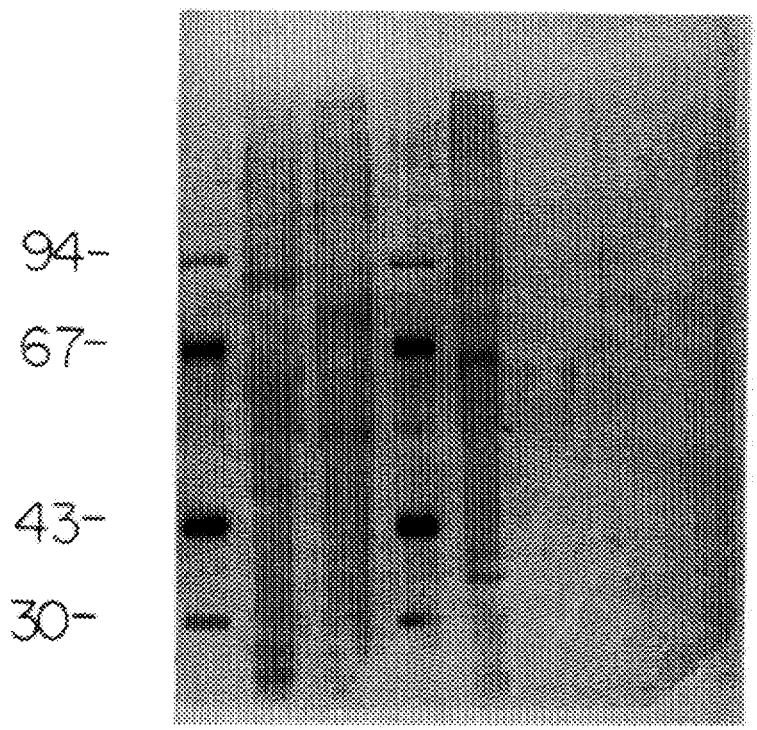
FIG. 5 shows an SDS-PAGE analysis of homogeneity of immunoaffinity-purified IFN-gamma receptor.

The results of the SDS-PAGE of the immunoaffinity-purified IFN-gamma receptor are shown in FIG. 5, wherein aliquots of solubilized membrane receptor (lane C, 0.9 µg), immunoaffinity purified receptor (lane B, 0.6 µg), sample medium alone (lane D) and molecular weight markers (lane A), phosphorylase 94,000; bovine serum albumin 67,000; ovalbumin 43,000 and carbonic anhydrase 30,000) were electrophoresed in the presence of β-mercaptoethanol in polyacrylamide gel. Protein bands were visualized by silver staining.

TABLE III

| | Immunoaffinity chromatography of placental IFN-gamma receptor | | | |
|---|---|---|---|---|
| Step | Protein (mg) | $^{125}$I-IFN-gamma binding (pmol) | Specific activity (pmol/mg) | Purification (fold) |
| Solubilized membranes | 140.6 | 0.58 | 0.004 | — |
| Eluate (fractions 1–3) | 0.02 | 0.34 | 17 | 4250 |

The binding of radiolabeled IFN-gamma to a soluble receptor for the monitoring of the purification method was performed as follows: Aliquots (20–40 µl) of the solubilized receptor from various purification steps were mixed with $^{125}$I-IFN-gamma (250 units) either with or without labeled IFN-gamma (100,000 units) in PBS containing 0.1% BSA (200 µl). The mixture was incubated for 2 hours at 4° C., rabbit IGg (0.1% in PBS, 0.5 ml) was then added, followed by PEG-8000 (22% in PBS, 0.5 ml). The mixture was left for 10 minutes at 4° C. and then passed through a 0.45 µ filter (25 mm HAWP, Millipore). The filters were washed with cold PEG-8000 solution (8% in PBS), and counted. Background counts were determined in the presence of excess unlabeled IFN-gamma and were subtracted. Binding is expressed in pmoles of $^{125}$I-IFN-gamma.

EXAMPLE 8
Analysis by Western Blotting

Samples of affinity-purified receptor (500 ng/slot) were analyzed by SDS-PAGE under reducing conditions and electroblotted onto nitrocellulose sheets (BA 85, Schleicher and Schuell) at 60 volt, 250 mA in 25 mM Tris HCl/10 mM glycine buffer (pH 8.5)/20% methanol for 2 hours at 4° C. After electroblotting the nitrocellulose sheet was incubated overnight with 5% non-fat milk in PBS containing 0.05% Tween-20 and 0.02% sodium azide (blocking buffer). The nitrocellulose was incubated for 2 hours at room temperature with a mixture of the three anti-IFN-gamma receptor monoclonal antibodies (immunoglobulin fraction of ascitic fluids 10 mg/ml diluted with 1:150 in the blocking buffer). Following washings in 0.05% Tween-20 in PBS, the nitrocellulose sheet was incubated for 3 hours at room temperature with $^{125}$I-goat anti-mouse serum ($0.7\times10^6$ cpm/ml, in the blocking buffer). The sheet was then washed, dried and autoradiographed.

Western blotting of the load fraction, effluent and eluate was performed. Analysis of an aliquot from the load fraction which consisted of solubilized placental membranes revealed a single band of molecular weight 88,000. When this membrane preparation was passed on the immunoaffinity column, the 88,000 band could not be detected in the effluent fraction.

EXAMPLE 9
Isolation of cDNA Clones Encoding IFN-gamma Binding Proteins from HeLa Cells cDNA Library $1\times10^6$ recombinants of different inserts from a cDNA HeLa library in lambda gt11 (Clontech Laboratories, Inc. U.S.A) were screened with the aid of anti-IFN-gamma receptor monoclonal antibodies. Phages were absorbed to *Escherichia coli* strain Y1090, plated at a density of 25,000 p.f.u./9 cm petri dish and grown at 42° C. for 4 hours. 30 minutes after transfer of plates to 37° C., nitrocellulose filters previously soaked in 10 mM isopropylthiogalactosidase (IPTG) were overlaid on plaques and further incubated for 6 hours at 37° C., after which a second filter was applied for 10 hours.

Figure 6:
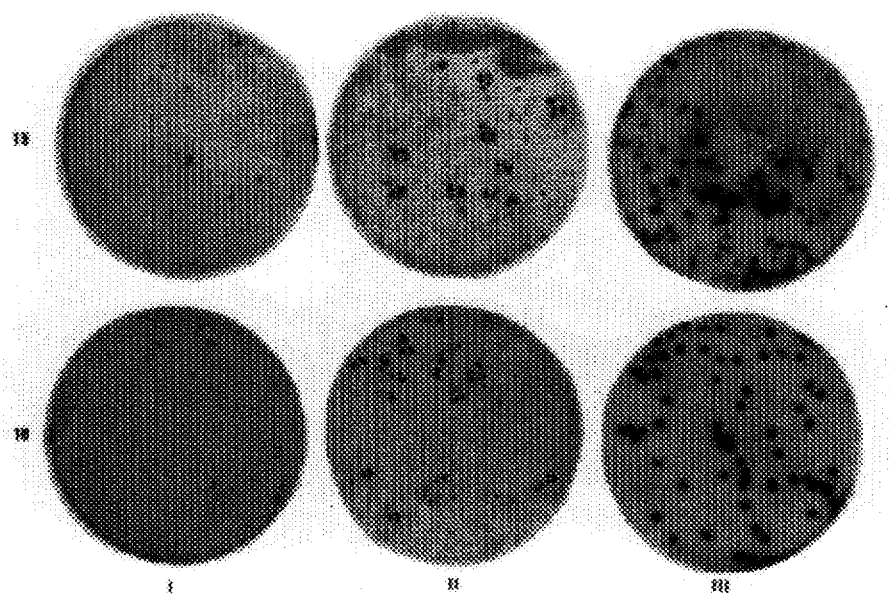
FIGS. 6A–B show (A) screening of a cDNA HeLa expression library and (B) subcloning of a positive clone.

Filters were marked and transfered to 10% low fat milk (1%), 0.05% Tween 20 in PBS for blocking (2 hrs at room temperature). The two sets of filters were washed in PBS containing 0.05% Tween 20 and incubated with monoclonal anti-IFN-gamma receptor antibodies obtained in Example 3 (monoclonal antibody 177-1 was preferably used), (20 μg/ml in blocking solution) for 3 hrs at room temperature. The filters were washed 5 times with PBS-Tween and positive clones were identified by $^{125}$I-goat anti-mouse F(ab)2 ($7\times10^5$ cpm/ml in blocking solution) following an overnight incubation at 4° C. and extensive washings with PBS-Tween. Positive clones were picked into 1 ml TMG (10 mM Tris-HCl, pH 7.5, 1 mM Mg SO4, 0.02% gelatin) containing 100 μl of chloroform and the phages were further subcloned by the same procedure described above. In FIG. 6, FIG. 6A shows the screening of a cDNA HeLa expression library and FIG. 6B shows the subcloning of a positive clone. DNA stocks were prepared from 500 ml *E. coli* 1088 infected with positive phages. DNA was purified by CaCl gradient followed by phenol-chloroform extraction.

EXAMPLE 10
Characterization of the Isolated Clones from HeLa Cells cDNA Library The purified lambda gt11 DNA containing positive cDNA clones were digested with EcoR1 and size-fractionated on 1% agarose gel. Four of the clones had an insert size of 0.5 Kb and one was of 0.7 Kb. Probes were prepared from one of the 0.5 Kb clones (15-21-1) and from the 0.7 Kb clone (18-4-3), using the multiprime DNA labelling systems kits (AMERSHAM). The technique is based on the use of random sequence hexanucleotide to prime DNA synthesis on denatured template DNA at numerous sites along its length (Feinberg A. P. and Vogelstein B., A Technique for radiolabelling DNA restriction endonuclease fragments to high specific activity, Anal. Biochem. (1983) 132:6-13, and (1984) 137:266). Cross hybridization among the clones was checked by Southern blots using the above mentioned probes. The 0.5 Kb probe hybridized to all four 0.5 Kb clones but not to the 0.7 Kb clone, while the 0.7 Kb probe hybridized only to the 0.7 Kb clone.

The EcoRI insert of the 0.5 Kb clone 15-21-1 was subcloned in a Bluescript vector and *E. coli* TG1 competent bacteria were transformed therewith. This transformed bacteria was deposited with the Collection Nationale de Cultures de Microorganismes (C.N.C.M.), Paris, France, on 14.11.88 under the Budapest Treaty and it has the identifying characteristics C.N.C.M. I-815.

EXAMPLE 11
Screening of a Human Placenta cDNA Library with DNA Probes $1\times10^6$ recombinants from human placenta cDNA library in lambda gt11 (Clontech Laboratories Inc., U.S.A.) were screened with the aid of the abovementioned DNA probes prepared from the 0.5 Kb and 0.7 Kb clones (Example 10). Phages were adsorbed to *E. coli* strain 41088, plated at a density of 25,000 p.f.u/9 cm petri dish and grown at 37° C. overnight, 2 sets of nitrocellulose filters were overlaid and immersed in a tray containing DNA-denaturing solution. The filters were washed, fixed and prehybridized to allow non-specific sites to be saturated by unlabelled DNA. Then the filters were hybridized with the $^{32}$P-labelled probes overnight at 67° C., washed and autoradiographed. 10 positive clones were obtained and picked up. DNA from the positive clones was purified by CaCl and followed by phenol-chloroform extraction.

EXAMPLE 12
Characterization of the Isolated Clones from Human Placenta cDNA Library The purified lambda gt11 DNA containing positive cDNA clones were digested with EcoR1 and size-fractionated on 1% agarose gel. Nine of the clones isolated by the 0.7 Kb probe had an insert size 1.15–2.3 Kb and they all cross-hybridized, while one of the clones isolated by the 0.5 Kb probe had an insert size of 1.8 Kb and hybridized only to itself. Cross-hybridization was determined by Southern blots.

Figure 7:
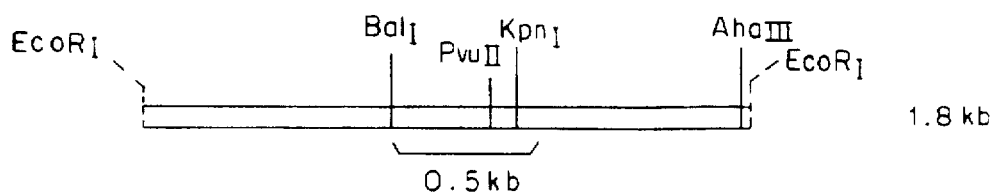
FIG. 7 is a restriction map of 1.8 kb cDNA fragment (No. 39) derived from a positive cDNA clone.

The clones were further characterized by digestion with restriction enzymes. The 1.8 Kb fragment (No. 39) was cut by restriction enzymes as shown by the restriction map of FIG. 7. A KpnI site was found at a distance of 1.1 Kb from the EcoR1 site of the lambda gt11 (19.6 Kb from the left end). A SacI site was found at a distance of 0.6 Kb from the EcoR1 site of lambda gt11. From a Southern blot experiment in which the 1.8 Kb fragment was cut by KpnI and run on a gel and the probe was the 0.5 Kb fragment (15-21-1), it was deduced that this 0.5 Kb fragment is located in a way that its KpnI site is near the right end of the lambda gt11.

Figure 8:
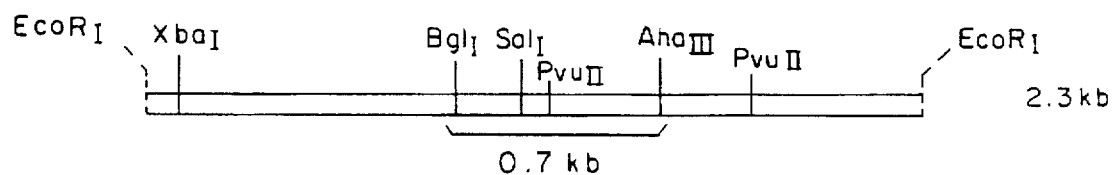
FIG. 8 is a restriction map of 2.3 kb cDNA fragment (No. 76) derived from a positive cDNA clone.

The 2.3 Kb fragment (No. 76) was cut by restriction enzymes as shown in the restriction map of FIG. 8. A SalI site was found in the middle of the 2.3 Kb insert. An XbaI site was found very near the EcoR1 site of the lambda gt11 (19.6 Kb from the right end).

EXAMPLE 13
Sequencing of the Clones

DNA of the 0.5 Kb, 0.7 Kb, 1.8 Kb and 2.3 Kb positive clones purified on CsCl gradient was cut by EcoR1 restriction enzyme. DNA of the Bluescript plasmid vector of Stratagens Cloning System (San Diego, Calif.) was cut as well by EcoR1, then dephosphorylated and run on a preparative agarose gel. The band of DNA was extracted from the gel phenol-chloroform extractions. Both the clone and the vector were now ready for ligation with the help of T4 ligase. *E. coli* (TG1) competent bacteria were used for transformation with the ligated vector. Vector was added to the bacteria at 4° C., followed by a heat shock (42° C.), removed to ice, then at room temperature and at 37° C. Finally the bacteria were plated on LB+Ampicillin (Amp). Colonies were picked and grown in LB+Amp. For sequencing, a single stranded DNA was prepared as follows: A starter of *E. coli* TG1 transformed bacteria with the ligated vector was grown in 2TY medium and Ampicillin followed by the addition of a helper virus. The DNA was precipitated by polyethylene glycol and extracted by phenol-chloroform. Finally the DNA was suspended in Tris-EDTA, ready for sequencing with the aid of the Sequenase Kit (USB).

FIG. 9 shows the nucleotide sequence of the 0.5 Kb cDNA segment and its translated amino acid sequence. FIG. 10 shows the complementary strand of the 0.7 Kb cDNA segment and its translated amino acid sequence. FIG. 11 shows two partial nucleotide and translated amino acid sequences of the 1.8 Kb cDNA segment. FIG. 12 shows partial nucleotide sequence of the 2.3 Kb cDNA and FIG. 13 a partial translated amino acid sequence thereof.

EXAMPLE 14
Preparation of Lysogen's Protein Lysates (from Hela Cells)

The technique used is described in *DNA cloning, A Practical Approach*, Vol. 1, Ch. 2, Edited by D. M. Glover, IRL press.

1) Generation of a lambda gt11 recombinant lysogen in *E. coli* Y1089. *E. coli* Y1089 cells were grown to saturation and infected with the lambda gt11 recombinant phage containing the 0.5 Kb clone described above (15-21-1) at 32° C. The cells were plated and incubated at 32° C. (at this temperature, the temperature-sensitive phage repressor is functional). Single colonies were tested for temperature sensitivity at 42° C. Cells from single colonies were spotted onto two plates: one plate was incubated at 42° C. and the second at 32° C. Clones which grow at 32° C. but not at 42° C. are lysogens.

2) Preparation of a crude lysate from lambda gt11 recombinant lysogen LB Medium was innoculated with a single colony of the *E. coli* Y1089 recombinant lysogen (15-21-1) and grown at 32° C. When the optical density of the culture at 600 nm was 0.5 the temperature was rapidly increased to 42° C. and incubated at 42° C. for 20 min. Then IPTG was added to a final concentration of 10 mM and the culture was incubated for 75 min at 37° C. The cells were harvested by centrifugation, suspended in a protein buffer (10 mM Hepes, 150 mM NaCl, 0.1% Triton X-100, 1 mM PMSF and 20 TIU Aprotinin) and frozen in liquid nitrogen. Following first thawing lysosyme was added to a final concentration of 0.3 mg/ml and DNase was added to a final concentration of 5–10 µg/ml. By repeating quick thawing and freezing three times a complete lysis of the induced lysogen was obtained. The resulting crude extract was spun before application on an immunoaffinity column.

EXAMPLE 15
Immunoaffinity Chromatography of the Crude Lysates

Figure 14:
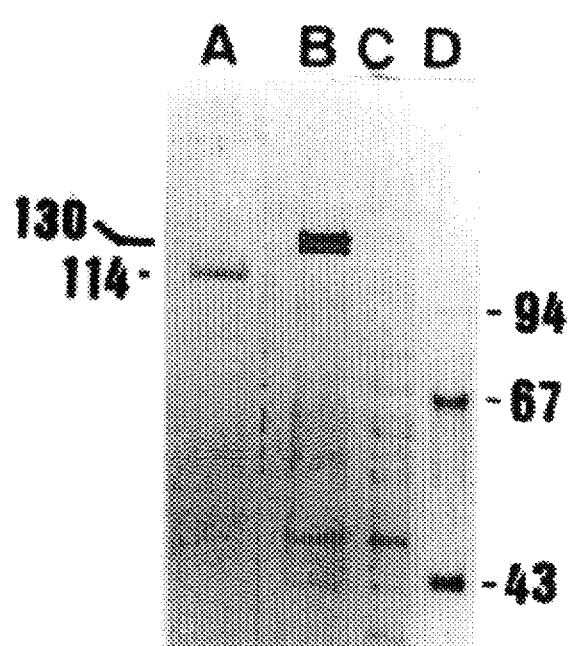
FIG. 14 is a gel showing results of an immunoaffinity purification of the recombinant protein.

An immunoadsorbent was prepared as in Example 7. The crude *E. coli* extract obtained in Example 14 (100 mg of the lysogen) was spun (10.000×g) and the supernatant was applied to the antibody column (3 mg Igs/0.3 ml agarose) at 4° C. The column was washed with PBS containing 0.1% Triton X-100 and eluted by citric acid (50 mM, pH 2) containing 0.05% Triton X-100 and 0.02% sodium azide. Five 0.5 ml fractions were collected into HEPES buffer (1M, pH 8.5) and kept at 4° C. Fractions No. 1 and No. 2 contained 75% of the eluted protein. Analysis of the purified lysate preparation by SDS-PAGE under reducing conditions and silver staining revealed the presence of a major band corresponding to a molecular weight of about 130,000 (the molecular weight of β-galactosidase is 114,000). The results are shown in FIG. 14: Lane A - β-galactosidase; Lane B - lysate elution fraction; Lane C - load fraction (crude lysogen); Lane D - molecular weight markers.

EXAMPLE 16
Western Blotting

Figure 15:
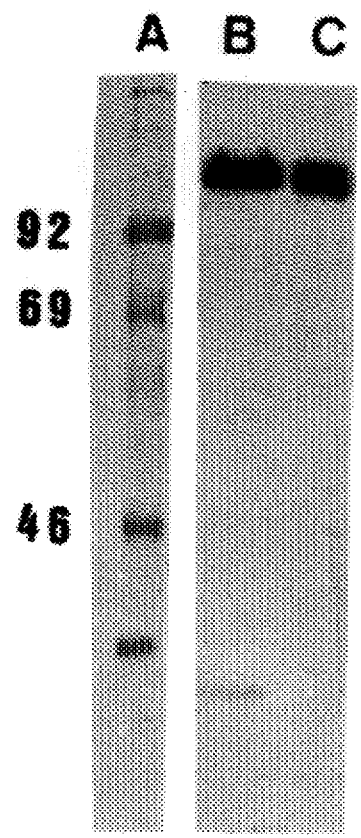
FIG. 15 is a western blot demonstrating the presence of the recombinant protein in E. coli lysates.

Samples of either crude *E. coli* extracts containing the induced fused protein (100 µg/slot) or of affinity-purified fused protein (1 µg/slot) were analyzed by SDS-PAGE under reducing conditions and electroblotted onto nitrocellulose sheets at 60 volt, 250 mA in 25 mM Tris HCl/10 mM glycine buffer (pH 8.5)/20% methanol for 2 hrs at 4° C. After electro-blotting the nitrocellulose sheet was incubated overnight with 10% non-fat milk in PBS containing 0.05% Tween-20 and 0.02% sodium azide (blocking buffer). The nitrocellulose was incubated for 2 hrs at room temperature with anti-IFN-gamma receptor monoclonal antibodies (immunoglobulin fraction of ascitic fluids 10 mg/ml diluted 1:500 in the blocking buffer). Following washings in 0.05% Tween-20 in PBS, the nitrocellulose sheet was incubated overnight at 4° C. with $^{125}$I-goat anti-mouse serum (0.7×10$^5$ cpm/ml in the blocking buffer). The sheet was then washed, dried and autoradiographed. As shown in FIG. 15, a band of Mr of about 130,000 was obtained both in the crude and the affinity purified fractions. In FIG. 15: Lane A - molecular weight markers; Lane B - Immunoaffinity purified lysogen; Lane C - crude lysogen.

Figure 16:
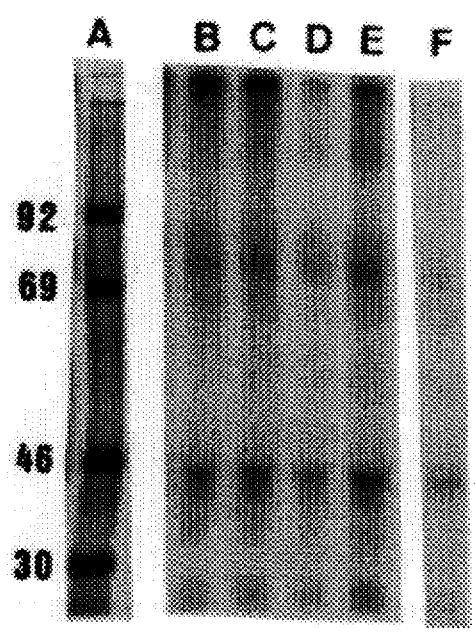
FIG. 16 is a gel showing the cross-linking of IFN-γ to the recombinant receptor.

EXAMPLE 17
Cross-Linking of Radiolabelled $^{125}$I-IFN-Gamma to the Fused Protein Preparations of the affinity purified fused protein (3 µg) or of pure β-galactosidase were mixed with $^{125}$I-IFN-gamma (1000 units, 5×10$^5$ cpm) in the presence or absence of unlabelled IFN-gamma (1000 fold), and the mixture was left for 2 hrs at room temperature. Di Succinyl Suberate (DSS) was added to a final concentration of 0.3 mM. The cross linking was stopped after 15 min at 4° C. by the addition of 1M Tris-HCl buffer. The mixture was immunoprecipitated with rabbit anti-β-galactosidase serum (1:200, 2 hrs at room temperature), followed by the addition of Prot A Sepharose beads. The beads were washed twice with PBS containing 0.05% Tween 20 and once with PBS, suspended in a sample buffer and the supernatant was analyzed by SDS-PAGE followed by autoradiography. As demonstrated in FIG. 16, lane E, a complex of M.W.=155,000 was obtained when the fused protein coded by the 0.5 Kb clone was cross-linked to $^{125}$I-IFN-gamma. The band was abolished by the addition of an excess of unlabeled IFN-gamma (Lane D). No such band was observed when cross-linking was performed with pure β-galactosidase itself (Lane F). In FIG. 16: Lane A - molecular weight markers; Lanes B and C - pure lysogen (0.7 Kb) cross-linked to $^{125}$I-IFN-gamma in the presence or absence of an excess of unlabeled IFN-gamma, respectively; Lanes D and E - pure lysogen (0.5 Kb) cross-linked to $^{125}$I-IFN-gamma in the presence or absence of an excess of unlabeled IFN-gamma, respectively; Lane F - pure β-galactosidase cross-linked to $^{125}$I-IFN-gamma.

EXAMPLE 18
Expression of Clone 39 cDNA

Figure 17:
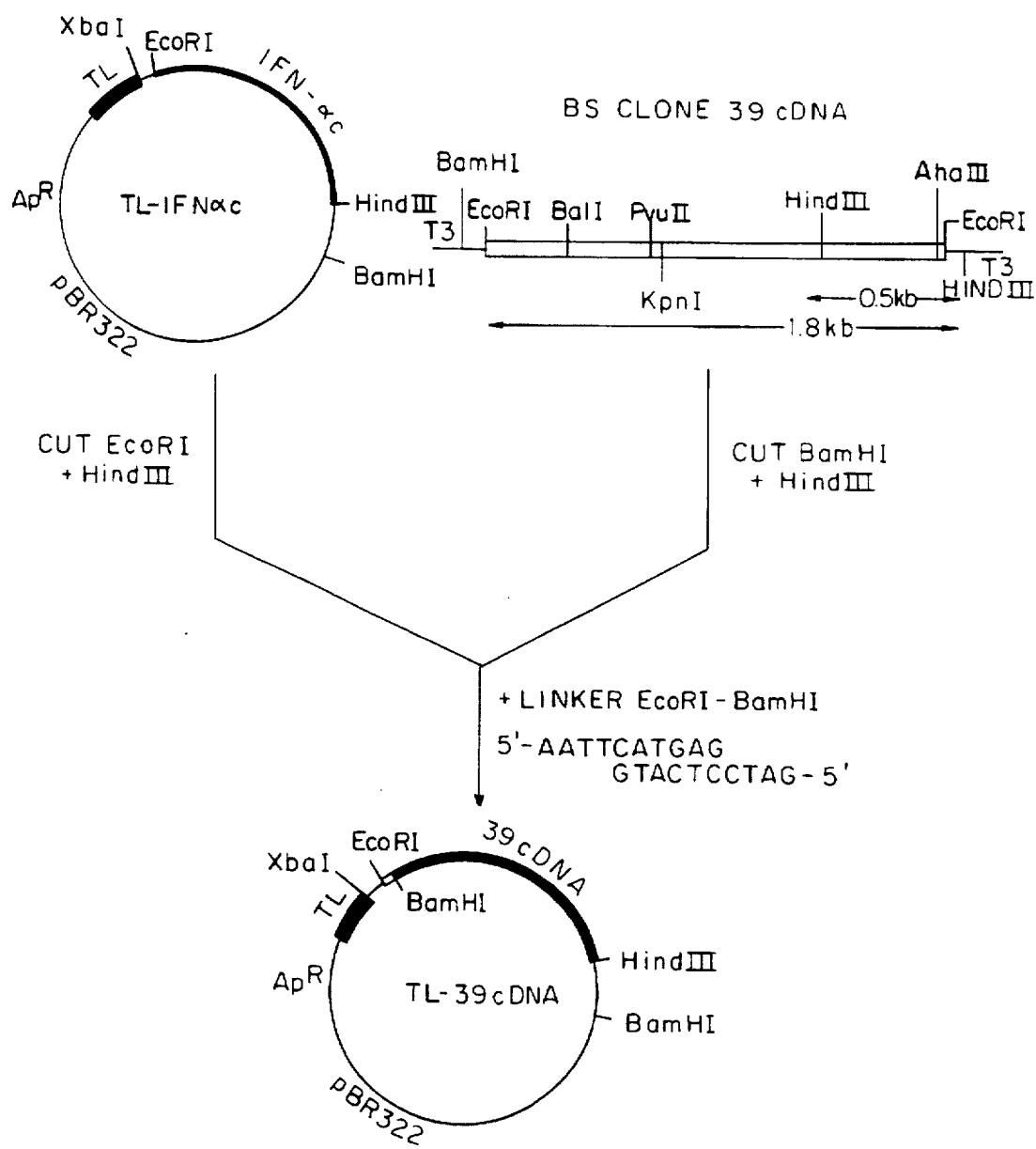
FIG. 17 is a scheme illustrating the construction of the TL-39cDNA plasmid.

The 1.8 Kb insert of lambda gt11 clone N 39 isolated from the human placenta cDNA library with the 0.5 Kb probe (as in Example 12) was cut out by EcoRI and inserted in the EcoRI site of the KS Bluescript vector (BS) from Stratagene Cloning Systems (La Jolla, Calif.). In the resulting BS-39cDNA, the orientation was such that the AhaIII site at the 3'-end of the sense strand of the 1.8 Kb insert (FIG. 7) is close to the HindIII site and T3 RNA polymerase promoter of the BS vector, whereas the 5'-end is close to the BamHI site and T7 RNA polymerase promoter of the BS vector (FIG. 17). As expression vector we used plasmid TL-IFN-αc described by Chernajovsky Y., et al. in Biochemical Engineering III, Annals N.Y. Acad. Sci., Vol. 413, pp 88–96, 1983. This plasmid which contains a tryp-lac promoter and a ribosomal binding site followed by an EcoRI site, was cut by EcoRI and HindIII and ligated with a synthetic EcoRI-BamHI linker (containing the initiator ATG) to the BamHI-HindIII fragment of BS-39cDNA to yield plasmid TL-39cDNA (FIG. 17). This construction adds 9 codons to the coding sequence of the 39 cDNA fragment. The TL-39cDNA plasmid was transfected into *E. coli* JM101 i and cultures were induced with isopropyl thiogalactosidase (IPTG) as described by Chernajovsky et al. (ibidem). Harvesting of the cells and extraction of the protein, immunoaffinity chromatography, western blotting and cross-linking of $^{125}$I-IFN-gamma were performed as in Example 14 to 17, respectively. For the cross-linking of $^{125}$I-IFN- gamma, either rabbit anti-IFN-gamma serum or mouse anti-IFN-gamma receptor monoclonal antibody are used for immunoprecipitation.

Figure 18:
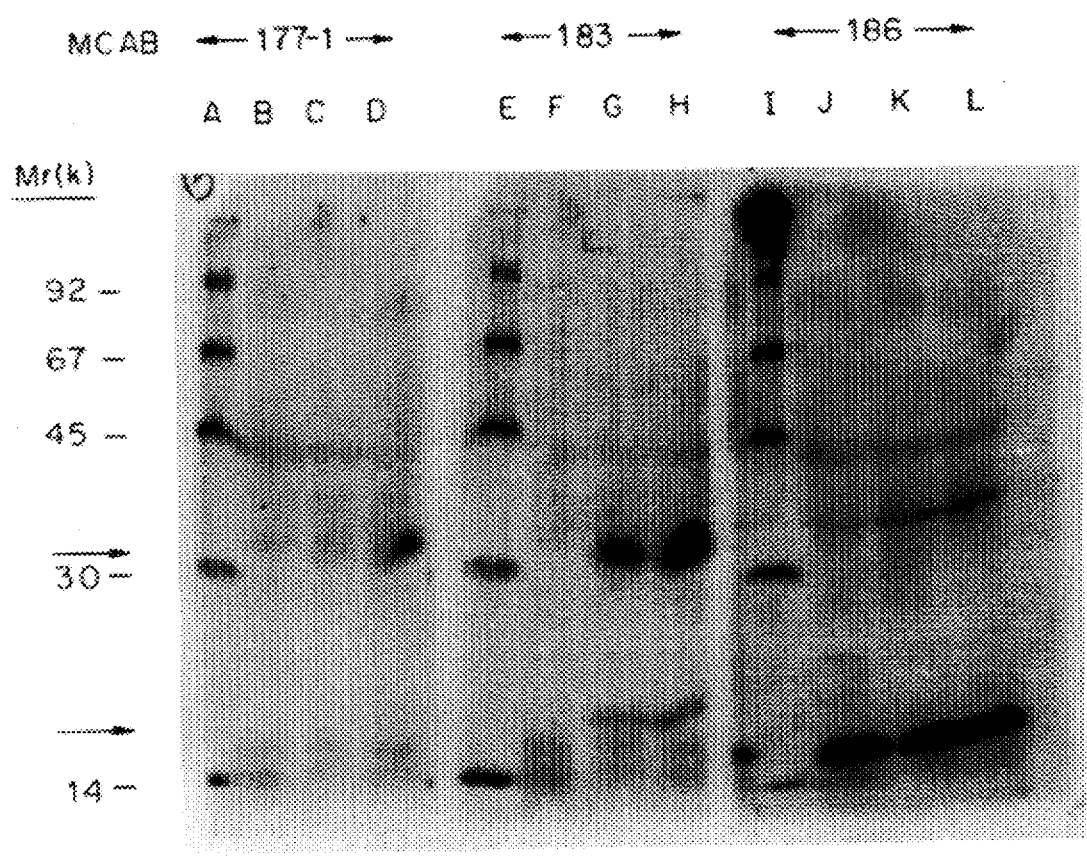
FIG. 18 shows the results of western blotting of cross-linked complexes of the TL-39cDNA expression product with three antibodies.

In FIG. 18: Lane A - Molecular weight markers; Lane B - Crude extract of non-induced bacteria No. 39. Lane C and D - Crude extract of IPTG-induced bacteria No. 39 after 60 min. and 45 min. of induction, respectively. Blot incubated with antibody No. 177-1. Lanes E-H - as A-D, but incubated with antibody No. 183. Lanes I-L - as A-D, but incubated with anti-IFN-gamma antibody (negative control). As shown in FIG. 18, a single band of Mr of 32,000 was obtained when the blot was incubated with antibody No. 177-1 (Lanes C and D). When the blot was incubated with antibody No. 183 a major band of Mr of 32,000 and a minor band of Mr of 17,000 were obtained (Lanes G and H).

The size of the protein may be smaller than that of the natural product of the 39 cDNA as only a fragment of this cDNA was used in the construct. This protein comprises the sequences shown in FIG. 11. The sequence of fragment BalI-Kpn I (FIG. 11B) comprises the sequence shown in FIG. 9.

EXAMPLE 19
Expression of Clone 76 cDNA

Figure 19:
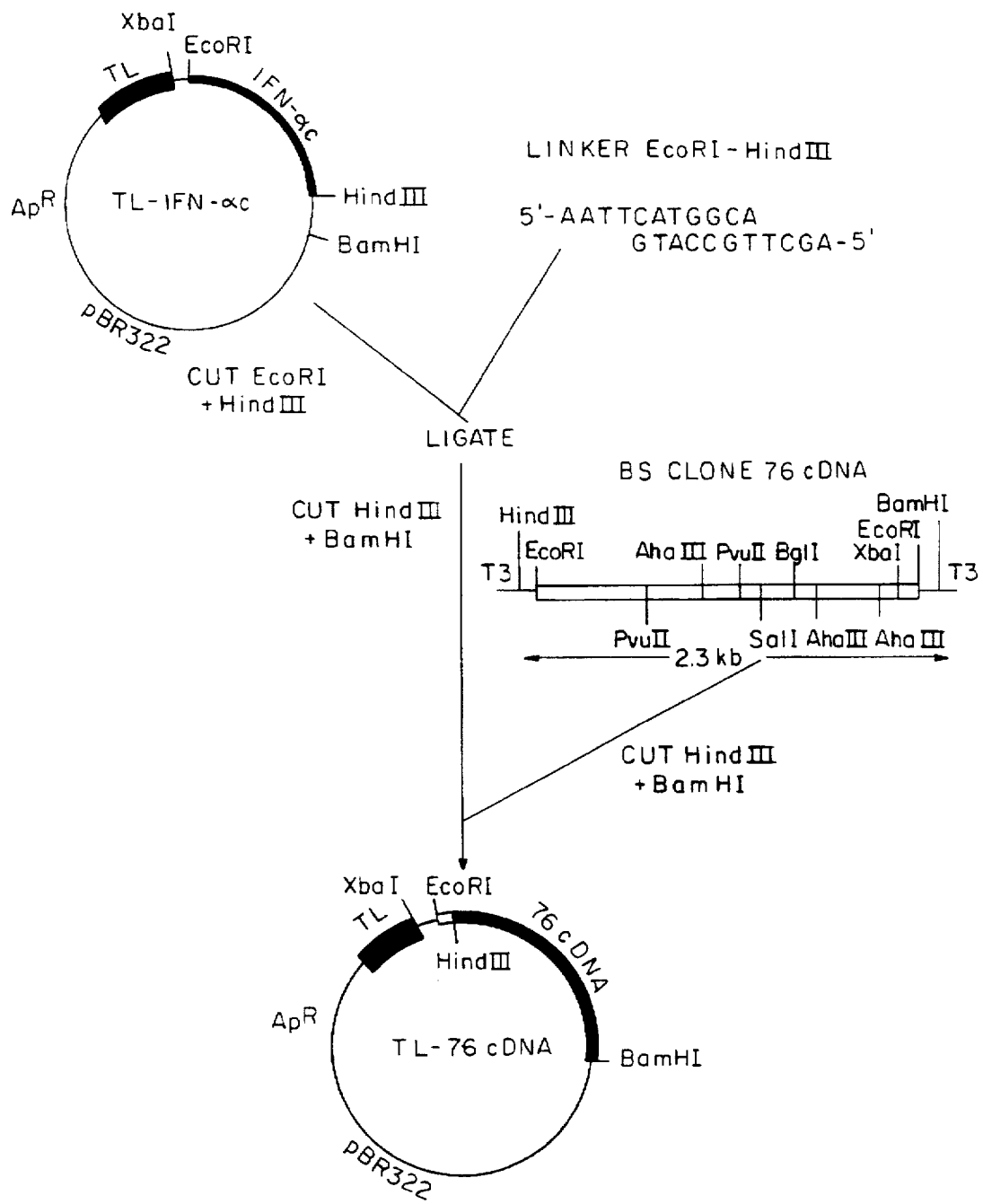
FIG. 19 is a scheme illustrating the construction of the TL-76cDNA plasmid.
Figure 20:
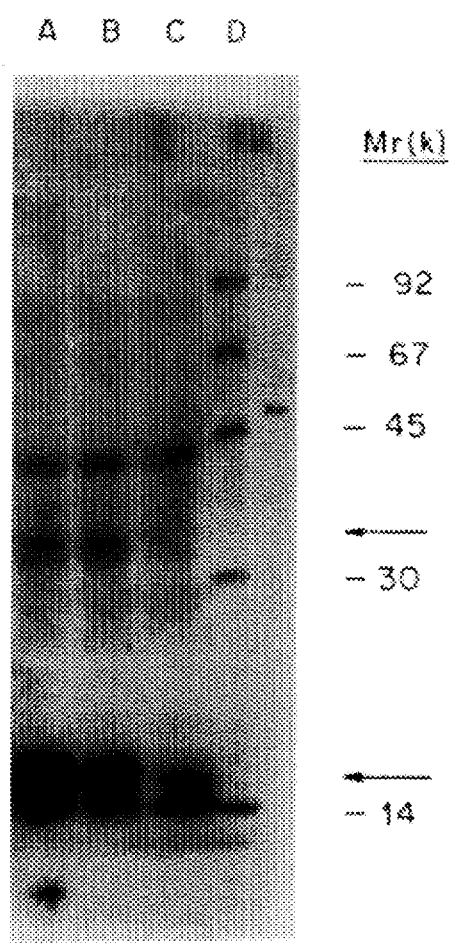
FIG. 20 shows a western blot demonstrating the expression of 17 and 32 kDa proteins in E. coli transformed with TL-76cDNA.

The 2.3 Kb insert of lambda gt11 clone N 76 isolated from the human placenta cDNA library with the 0.7 Kb probe (as in Example 12) was cut out with EcoRI and inserted in the EcoRI site of the KS Bluescript vector, so that the XbaI site at the 3'-end of the sense strand of the 2.3 Kb insert (FIG. 8) is close to the BamHI site and T7 RNA polymerase promoter of the BS vector whereas the 5'-end is close to the HindIII site and the T3 RNA polymerase promoter of the plasmid BS vector. The expression plasmid TL-IFN-αc was cut with EcoRI and HindIII and religated with a synthetic EcoRI-HindIII linker (FIG. 19). The resulting plasmid was recut by HindIII and BamHI and ligated to the HindIII-BamHI 2.3 Kb cDNA excised from the above BS clone 76cDNA to yield TL-76cDNA (FIG. 19). This plasmid was transfected into *E. coli* JM101 i and cultures were induced with IPTG. A 34,000 and a 17,000 Mr protein products were identified which reacted with monoclonal antibody 183 on immunoblots (FIG. 20). This protein comprises the sequence shown in FIG. 13. Extraction from the cell culture, immunoaffinity chromatography, Western blotting and $^{125}$I-IFN-gamma cross-linking were performed as above.

In FIG. 20: Lane A, B - Crude extract of IPTG-induced bacteria No. 76 after 120 min. and 180 min., respectively. Lane C - Crude extract of non-induced bacteria No. 76. Lane D - Molecular weight markers. Blot incubated with a mixture of antibodies No. 177-1 and 183.

As shown in FIG. 20, induced proteins of Mr of 17,000 and 32,000 were obtained when the blot was incubated with a mixture of antibodies No. 177-1 and 183 (Lanes A and B).

Utility and Compositions

The IFN-gamma binding proteins of the present invention, the proteins substantially homologous therewith or fragments thereof, can be used either alone or together for modulating the activity and protecting against the deleterious effects of IFN-gamma by systemic or local administration. They will be useful in the treatment of conditions wherein excess of IFN-gamma is endogenously formed or is exogenously administered. Thus, modulation of IFN-gamma activity by IFN-gamma binding protein is beneficial in cases of undesired production of endogenous IFN-gamma which may occur in local inflammation, systemic inflammation such as occuring in septic shock and in various autoimmune and inflammatory diseases, including but not restricted to rheumatoid arthritis, multiple sclerosis, juvenile diabetes at its onset, polymyositis, Behcet disease, thyroiditis, Lupus erythematosus and dermatitis. Modulation of IFN-gamma activity by the IFN-gamma binding proteins is also beneficial in cases of administration of exogenous IFN-gamma whenever side effects due to overdose or to patient's sensitivity to IFN-gamma is diagnosed. Alternatively the IFN-gamma binding proteins can be used to prolong or even enhance the antiviral, anti-inflammatory, anticellular or any other activity of both endogenous and exogenous IFN-gamma.

The protein of the invention can be formulated according to known methods to prepare pharmaceutically useful compositions in a mixture with a pharmaceutically acceptable carrier vehicle. Suitable vehicles and their formulations are described, for example, in Remington's *Pharmaceutical Sciences* by E. W. Martin.

The pharmaceutical compositions of the invention are prepared for administration by mixing the protein with physiologically acceptable carriers, stabilizers and excipients, and prepared in dosage form, e.g. by lyophilization in dosage vials. The amount of active compound to be administered will depend on the route of administration, the disease to be treated and the condition of the patient. The way of administration can be via any of the accepted modes of administration for similar agents and will depend on the condition to be treated.

Strands of the DNA molecules of this invention and fragments thereof may be used as hybridization probes for the isolation or identification of related nucleic acid sequences, in the same manner, e.g., the 0.7 kb probe was used to identify inserts of 1.15–2.3 kb as previously described.

We claim:

1. An isolated DNA molecule, comprising the nucleotide sequence of a cDNA molecule present in a human placental library, wherein a hybridization probe having the complement of one of the DNA sequences shown in FIGS. 9, 10, 11A, 11B, and 12 will selectively identify said cDNA molecule in said library, and wherein said cDNA molecule encodes an IFN-gamma-binding polypeptide.

2. An isolated and purified polypeptide which is capable of binding interferon-gamma and which comprises the amino acid sequence of the interferon-gamma-binding polypeptide encoded by a DNA molecule in accordance with claim 1.

3. A polypeptide in accordance with claim 2 which includes the amino acid sequence of FIG. 10.

4. A polypeptide in accordance with claim 2 which includes the amino acid sequence of FIG. 11A (the linker sequence noted therein being optional).

5. A polypeptide in accordance with claim 2 which includes the amino acid sequence of FIG. 11B.

6. A polypeptide in accordance with claim 2 which includes the amino acid sequence of FIG. 12 (the linker sequence noted therein being optional).

7. An isolated DNA molecule, comprising a DNA sequence encoding a polypeptide in accordance with claim 2.

8. A DNA molecule in accordance with claim 7, wherein said DNA sequence encoding a polypeptide is operably linked with an expression DNA sequence capable of effecting expression of said DNA sequence encoding a polypeptide in a suitible host cell.

9. A host cell transfected with the DNA molecule of claim 8, said expression DNA sequence being operable in said host cell.

10. A process for producing a protein which comprises, culturing a host cell according to claim 9 under conditions conductive to expression, and isolating the protein.

11. The DNA molecule of claim 1, wherein said cDNA sequence is operably linked with a DNA sequence capable of effecting expression of said cDNA in a suitable host cell.

12. A host cell transformed with the DNA molecule of claim 11.

13. A host cell according to claim 12, wherein the cell is a prokaryotic cell.

14. A host cell according to claim 12, wherein the cell is a eukaryotic cell.

15. A process for producing a protein which comprises culturing a transformant host cell according to claim 12 under conditions conducive to expression of the protein encoded by said cDNA, and isolating the protein.

16. An isolated DNA molecule, comprising the nucleotide sequence of a fragment of a cDNA molecule according to claim 1, wherein a polynuycleotide or oligonucleotide having the sequence of the complement of said fragment will specifically hybridize with said cDNA molecule in said library.

17. An isolated DNA molecule, comprising a fragment of the strand of the DNA sequence of FIG. 9 or FIG. 12 which is sufficiently long so as to hybridize to the complement of the DNA sequence of FIG. 9 or FIG. 12, respectively, under hybridization and wash conditions equivalent to those in which an 0.7 kb probe having the DNA sequence shown in FIG. 12 will selectively identify clones in a human placental cDNA library having insert sizes of 1.15–2.3 kb, said clones encoding all or part of a human IFN-gamma-binding protein.

18. An isolated and purified interferon-gamma binding polypeptide comprising the amino acid sequence of FIG. 9.

19. An isolated DNA molecule, comprising a DNA sequence encoding a polypeptide in accordance with claim 18.

* * * * *